(12) United States Patent
Miller (10) Patent No.: US 8,460,216 B2
(45) Date of Patent: Jun. 11, 2013

(54) SYSTEMS AND METHODS OF ANALYZING VIBRATIONS IMPARTED TO TISSUES AND TEETH

(75) Inventor: Ross John Miller, Sunnyvale, CA (US)

(73) Assignee: Bao Tran, Saratoga, CA (US)

( * ) Notice: Subject to any disclaimer, the term of this patent is extended or adjusted under 35 U.S.C. 154(b) by 219 days.

(21) Appl. No.: 12/951,893

(22) Filed: Nov. 22, 2010

(65) Prior Publication Data

US 2011/0159460 A1 Jun. 30, 2011

Related U.S. Application Data

(60) Provisional application No. 61/284,809, filed on Dec. 24, 2009.

(51) Int. Cl.
*A61B 5/117* (2006.01)
*A61B 5/103* (2006.01)

(52) U.S. Cl.
USPC ........................................... 600/590

(58) Field of Classification Search
USPC .......... 600/590, 587, 589, 462, 301; 433/215, 433/3, 72; 455/90.1; 340/573.1; 381/122, 381/94.1
See application file for complete search history.

(56) References Cited

U.S. PATENT DOCUMENTS

| | | | | |
|---|---|---|---|---|
| 3,094,115 | A | * | 6/1963 | Polin .............................. 600/462 |
| 5,518,008 | A | * | 5/1996 | Cucchiaro et al. ............. 600/590 |
| 5,680,874 | A | * | 10/1997 | Takuno ......................... 600/587 |
| 2009/0149722 | A1 | * | 6/2009 | Abolfathi et al. ............. 600/301 |

* cited by examiner

*Primary Examiner* — Brian Szmal
(74) *Attorney, Agent, or Firm* — Tran & Associates (57) ABSTRACT

Systems and methods are disclosed for performing dental diagnostics by inducing vibrations in a first dental object using a vibratory transducer; picking up at a receiver vibrations transmitted by the vibratory transducers; capturing vibrations from an second dental object and comparing the captured vibrations against a database of known dental characteristics; and generating a dental diagnostic.

20 Claims, 5 Drawing Sheets

SYSTEMS AND METHODS OF ANALYZING VIBRATIONS IMPARTED TO TISSUES AND TEETH

The present application claims priority to Provisional Application Ser. No. 61/284,809, filed on Dec. 24, 2009, the content of which is incorporated by reference.

FIELD OF THE INVENTION

The invention relates to dental diagnostic and therapeutic applications using vibrations.

BACKGROUND OF THE INVENTION

Diagnostics is one area in dentistry in which enhanced skills continue to be needed. The main dental diagnostic tool, the dental explorer or probe, has been the mainstay in dental technology for diagnosing caries for over 150 years. Current methods of clinical examination include visualization and touch with the explorer. Both, however, can give false information. Currently, dentists tap on the teeth with the end of the dental explorer instrument to put a vibration into a tooth. By comparing the sounds these vibrations make a dentist can assess various conditions. A dentist can usually tell by the sound transmissions of these vibrations that something is not quite right. So much is based on the dentist's experience of listening and feeling of these vibrations. It is very subjective.

X-rays have been considered state of the art, but do not allow for early detection of incipient lesions. For example, leakage around the periphery of a filling cannot always be checked adequately with these methods. Further, these methods have not always proved satisfactory as to ascertaining the quality of tooth structure in all types of cavities, including Class I, II, III, IV, V, VI, and some types not classified in these groups such as crown margin caries, and intracanal caries. Although the current method of choice in dentistry to diagnose inter-proximal decay is with x-rays or radiographic interpretation, even given ideal circumstances, it has been shown that x-ray diagnosis is correct only about 30% of the time. Indeed, these methods are difficult for the inexperienced practitioner to achieve success as it generally requires years of clinical experience to master x-ray interpretation.

Ultrasonic devices have been used to detect smooth surface lesions (U.S. Pat. No. 6,162,177), jawbone cavitations (U.S. Pat. No. 6,030,221) and to evaluation root canal treatment (U.S. Pat. No. 5,115,813). For example, U.S. Pat. No. 7,175,599 discloses a method of diagnosing a subject by delivering ultrasound signals using shear waves includes applying a portion of an ultrasound mainbeam to a bone surface at an incident angle relative to the surface of the bone to induce shear waves in the bone, energy in the shear waves forming a substantial part of energy of first ultrasound waves at a desired region in the subject through the bone, detecting at least one of reflected and scattered energy of the applied ultrasound mainbeam, and analyzing the detected energy for a diagnostic purpose. However, such approach is expensive and not always possible due to skull geometry.

United States Patent Application 20030044755 discloses dental diagnosis by exploring a tooth surface or tooth material of a patient with a dental tool applying a known DC voltage to a localized region of the tooth surface area to locate a treatment area indicated by either a local lower resistance area surrounded by a higher resistance area, or a local higher resistance area surrounded by a lower resistance area; allowing for the assimilation of additional information needed for advanced treatment of the area being tested; verifying successful treatment of the treatment area by applying the dental tool with the known DC voltage to the treatment area and confirming the presence or absence of the local lower or higher resistance area; and permitting continuation of testing of the treatment area or a new treatment area, based upon those new findings. However, applying large electrical currents to human may not be safe, particularly if the patient is wearing pacemakers.

SUMMARY

In one aspect, systems and methods are disclosed for performing dental diagnostics by inducing vibrations in a first dental object using a vibratory transducer; picking up at a receiver vibrations transmitted by the vibratory transducers; capturing vibrations from an second dental object and comparing the captured vibrations against a database of known dental characteristics; and generating a dental diagnostic.

In another aspect, a method of acquiring internal and external structures of dental tissues and restorations includes emitting vibrations and analyzing the response of those vibrations utilizing a database of known responses of different types of tissues, restorations and disease states.

In yet another aspect, a diagnostic system includes a solenoid or transducer for emitting vibrations into the surrounding tissues; a means by which the solenoid is attached to the teeth; a power source for activating the movement of the solenoid; an amplification means for changing the frequency of solenoid; a transducer for picking up vibrations from the dental components; a computer data base of known restorative, disease and healthy states; a software means of comparing vibrations to data base, a computer means for converting data into interpretable displays.

Advantages of the preferred embodiments may include one or more of the following. By using the disclosed data analysis method, a dental office can add a new method of collecting and analyzing patient information. Patients can be assured that there is quantitative, objective information. For most dental conditions, a vibration pattern can be obtained and compared against known dental conditions. The system supplies adjunctive information by which the dental practitioner may make a better decision regarding treatment alternatives. The system helps practitioners in determining if teeth or tooth structure is cracked, from disease or overloading; locating perforations through a tooth during root canal therapy, or during restorative procedures; determining key locations to place pins so as to select areas that will minimize the chance of cracking the tooth, or to minimize the possibility of causing nerve damage; determining, once a pilot hole has been made, whether a frank opening into the nerve has inadvertently been made; testing sealants for leakage or decay; and identifying hidden pit caries. The system can establish objective readings or findings which can be used as a baseline recorded in a patient's chart for future comparisons. The system can be used to help differentiate between enamel, dentin, sclerotic dentin, reparative dentin, thin or weak dentin, carious pulp exposures, iatrogenic pulp exposures, perforations, major canals, accessory canals, cracks, fissures, craze lines (and their length, direction and potential for problematic cause). The system also can determine if a filling material, base or cement had been adequately cured or sealed, prior to conclusion of a treatment. The system can work with or obviate the need for x-rays while providing superior diagnosis of dental conditions. Appropriate measurement yields tremendous information to the dentist. This information improves diagnosis, aids in better treatment, and allows for earlier detection of problems.

DESCRIPTION

Figure 1:
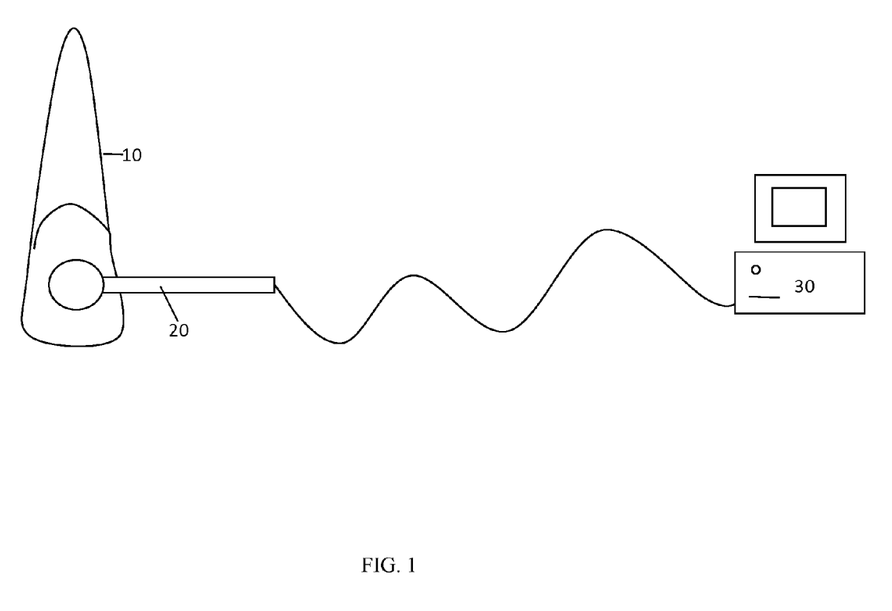
FIG. 1 shows an exemplary system to diagnose dental problems using vibrations.

FIG. 1 shows an exemplary system to diagnose dental problems using vibrations. The dental diagnostic system for analyzing tooth structure, restorative materials within a tooth structure, and disease states of a tooth includes a probe 20 which may be attached to a variety of dental probes, dental drills, and instruments to afford adaptability to a variety of clinical situations in providing diagnostic information on an object 10 such as a naturally occurring tooth structure, man-made materials placed or found within the tooth structure, diseased or otherwise affected, infected or effected tooth structure, as well as tooth structure that has been eroded, worn by attrition, abraded, abfracted, fractured, crazed, broken or otherwise compromised through patient use, misuse, fatigue or longevity of use. The probe 30 generates electrical outputs which are interpreted by a computer 30.

In one embodiment, the probe 20 can be a vibratory transducer that sends out vibrations at known frequency and amplitude. The probe 20 also includes a receiver which can be an accelerometer, for example. The accelerometer is attached to the teeth and connected to a computer. The accelerometer digitizes the received vibrations and provides them into the computer 30.

The transducer can be a single piezoelectric transducer or an array with elements arranged to fit in a mouthpiece or an appliance to be worn over the oral arch. The transducer elements can be mounted in silicone rubber or other material suitable for damping mechanical coupling between the elements. Other materials may also be used for the array construction. For example, the transducer may be formed from one or more pieces of piezocomposite material, or any material that converts electrical energy to acoustic energy. The receiver can also be positioned to fit in the mouthpiece or appliance. One embodiment of the receiver is an accelerometer, but a suitable piezoelectric transducer can serve as the receiver as well.

The software in the computer 30 compares these inputs to known vibration responses corresponding to diseased states. The computer 30 displays a response on the computer screen for that patient. If there are multiple disease states, each state will be displayed. If there are ambiguous outcomes, probabilities will be given.

The probe 20 is placed between the teeth of a patient and the patient will be asked to bite down on the probe. Vibrations generated by the sound transducer will move through the tissues into the tooth or object 10 being analyzed. In one embodiment, the transducer in the probe 20 will vibrate between 10-600 Hz and create a pulse of vibration that conducts through the teeth, gums and bones of the skull. As the patient bites down on the probe 20 with the vibrating transducer, a dentist or doctor will touch the receiver or pick up to an adjacent or nearby tooth and take a reading. The computer receives data from the pick up and compares the data to known readings from the database.

The probe 20 can cause the emitted vibration or sound to be sent along a line within the object 10, and to be scanned (e.g., moved methodically) about a broader region of interest in the object 10. The line through the object 10 taken by the vibration may change directions (e.g., at interfaces of varying acoustic impedance). The computer 30 can process reflected energy received by the probe 20 into an image based on the direction of the beam and the time between sending and receiving the vibratory energy. Also, the computer 30 does not have to process received energy to form an image of the object 10. The computer 30 can process the received energy to provide other diagnostic information, e.g., a binary indication of whether a void is detected (e.g., a cavity or abscess in a tooth or bone, such as a jaw bone), among others. The computer 30 can also process the information to form an image, e.g., of anatomy of the object 10, for example.

The mechanical direction/orientation of the probe 20 may be manually adjusted. Preferably, the angle of the surface of the object 10 is determined by sight, without the use of imaging equipment such as an X-ray, CT (computer tomography) or MR (magnetic resonance) scanner. Guides, however, may be provided for indicating when vibrations normal to the probe 20 will produce good vibrations in the object 10. Further, multiple vibration beams may be produced simultaneously from the probe 20 directed at different locations, and of similar or different frequency and/or amplitude.

For various conditions such as cracked teeth, broken fillings, cavities, and abscesses, the vibrations found in teeth upon tapping will be different. The vibrations travel down the lengths of the teeth and bounce off the bone and create resonances and damping at different frequencies, depending on what structures are being vibrated. Soft tissue and hard tissues of different types can be recognized. Ideally, the data picked-up can:

Identify different types of teeth: Central Incisors, Lateral Incisors, Canines, Bicuspids and Molars.

Identify different types of dental materials: Composite, Amalgam, Gold, Porcelain, Porcelain bonded to metal, posts, Endodontics, Implants and others.

Different disease states of the teeth: Carries, Ankylosis, mobility, abscesses, bone loss, necrosis and others.

All states of the teeth have their own unique vibration qualities.

Figure 2:
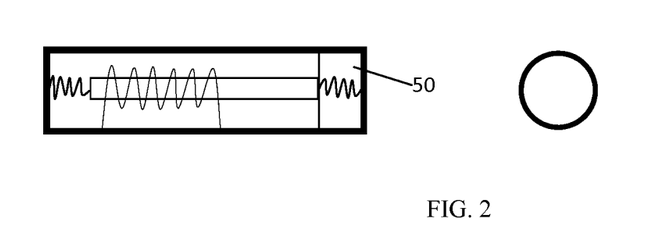
FIG. 2 shows an exemplary vibration unit that will be placed between the teeth.

One embodiment of the inventive dental diagnostic system includes a stand-alone device as well as a device together with a computer. In some embodiments the device and the computer will provide output indicative of the tooth's condition. In other embodiments, using the auxiliary display, the device need not have its own output device. An exemplary stand-alone vibratory transducer is shown in FIG. 2. A transducer 50 imparts the vibration to the teeth. The vibratory transducer 50 is held between the teeth by the patient. In one embodiment, a single transducer would emit a vibration through a single tooth in the lower and upper arch. Those vibrations would be transmitted through the teeth and bone. The vibration would bounce off all the structures and slowly dissipate. The receiver or pick up device would receive the vibrations and a processor in the stand-alone device would then compare the vibrations and dissipations to a known database. That database would contain known tooth states, restoration information and disease states. In one implementation, the transducer 50 is a solenoid device with a diaphragm which can be tapped against by a rod suspended by springs. Its frequency can be adjusted through a dial so the dentist can adjust the frequency range.

Figure 3:
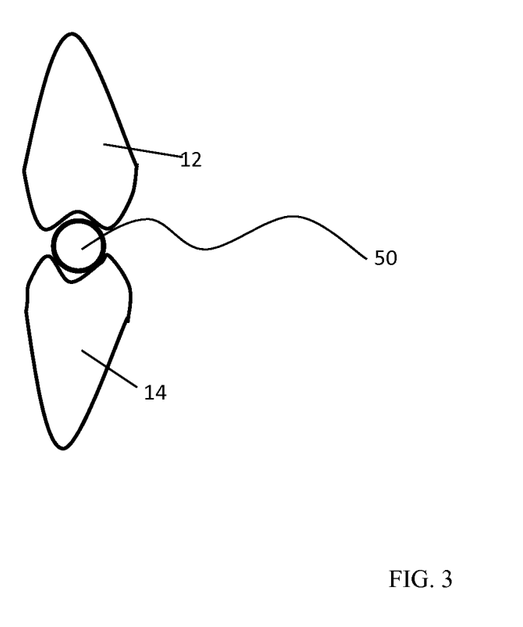
FIG. 3 shows an exemplary vibration device between the teeth.

FIG. 3 shows the transducer 50 held between the teeth. Ideally these teeth will be of known quality. That is, the teeth will be healthy teeth, although such condition is not absolutely required. The transducer 50 can be held against teeth by the dentist, but it may be easier to have the patient hold the transducer 50 against the teeth while the dentist applies the receiver or pick-up unit on another tooth.

Through familiarity with the use of the device, a practitioner would be able to analyze a myriad of dental conditions involving tooth structures, materials within a tooth structure, disease states of teeth, as well as to aid the practitioner in proper choice of methods of treatment of those conditions. A further realm of dentistry not yet completely investigated involves the science of materials. In conjunction with the use of the device, and specially designed materials, it would be possible to analyze materials before, during and after they are placed into teeth.

Figure 4:
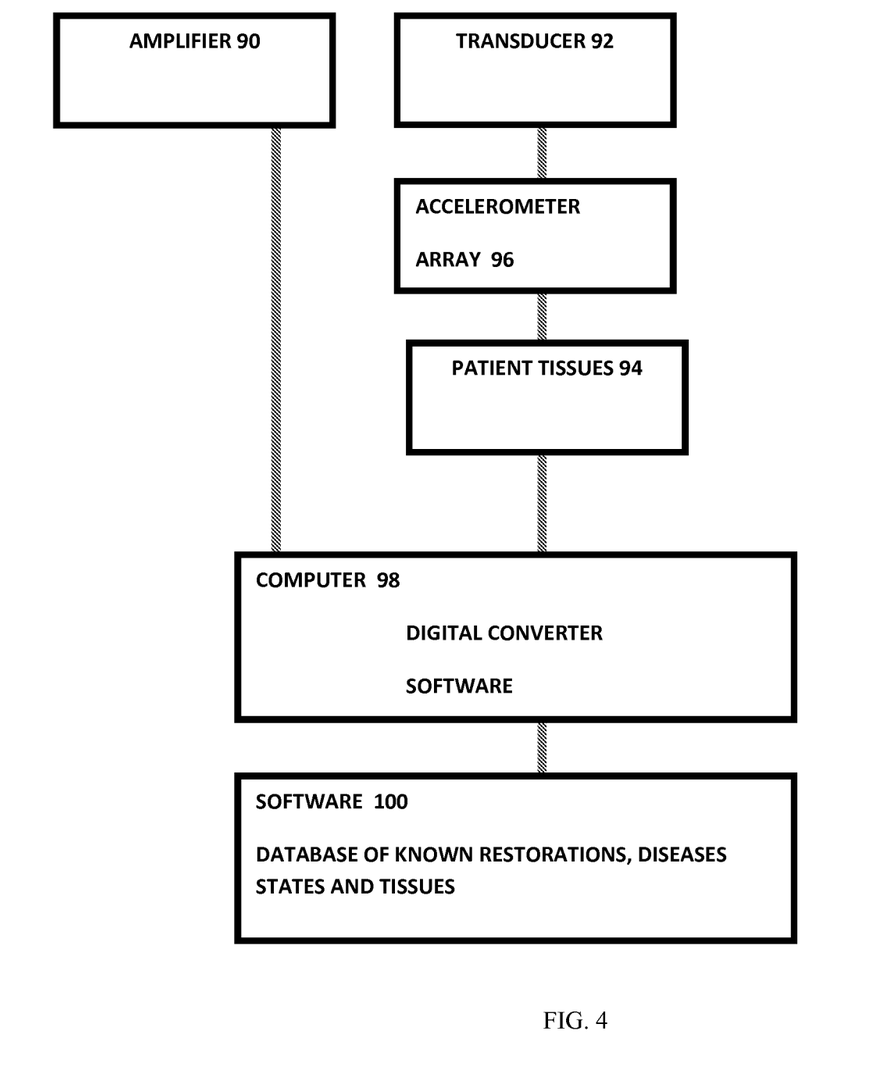
FIG. 4 shows an exemplary schematic block diagram of the instrumentation of the diagnostic device.

FIG. 4 shows in more details the computer 30 and the interface to the probe 20. An amplifier 90 amplifies vibratory output from a transducer 92. A pick up unit having an accelerometer (or an array) 96 receives reflected vibrations from patient teeth or tissues 94. A computer 98 includes a digital converter to digitize output from the pick-up unit and software on the computer 98 can process the captured diagnostic data. Diagnostic software 100 can include a database of known restorations, diseases, and tissue conditions whose signatures can be matched against the capture diagnostic data, and the result can be displayed on a screen for review by the dentist.

Included in one embodiment of the instrumentation is the transmitter or transducer, which will emit the vibrations that will be imparted to the teeth and jaws. This will be connected to a power supply and amplifier, which will allow for a frequency range. On electrical excitation, the transducer emits an outgoing vibration. That vibration will then travel into the crown of the tooth and down is root into the soft tissues and out into the bones of the jaws.

The accelerometer or detector will be placed on the tooth of interest. It will receive the vibrations from the emitter. The effect of the vibrations on the tooth of interest will generate a pattern of frequency vibrations. Those vibrations will be digitally converted and analyzed against known dental states in the software of the computer. An important part of the invention is a database of known dental states.

As the data is collected various linear samplings and comparisons will be made against the database. Software will make these comparisons as the data is received from the teeth.

In operation, referring to FIG. 5, with further reference to FIGS. 1-4, a process 110 for performing diagnostics on, and/or providing therapy to, an object using the system 10 includes the stages shown. For exemplary purposes, the object is assumed to be a tooth as shown in FIG. 1, although this is exemplary only and not limiting to the scope of the invention. The process 110, is exemplary only and not limiting, and may be altered, e.g., by having stages added, removed, or rearranged.

Structures of the body can be visualized in many different ways. One of those ways is utilizing vibrations. If one taps on one's teeth or bones, one can clearly hear and feel a vibration. Teeth are particularly susceptible to vibration by having the unique quality of being the only tissues directly inside of bone. Once a vibration is imparted into a tissue, that tissue vibrates back and forth, which allows certain information to be gathered regarding the health status of that tissue. The teeth are again in a unique position for this type of diagnosis, being directly available to the touch and having a variety of dental restorative materials being placed directly in them. These vibrations travel differently through healthy and diseased tissues, soft and hard tissues, and various dental materials.

At stage 112, the probe 20 is positioned relative to the object 10. The vibration transducer may be positioned manually and/or by actuation of a positioner mounted on a frame and controlled by the computer 30. The probe 20 is positioned such that it can transmit sound energy to the surface of the tooth 10 to inject vibrations into the object 10. The desired positioning may be determined in accordance with the angle of the surface of the object 10 as determined visually by an operator of the system. The angle of the surface of the object 10 may also be determined by actuating the probe 20 and imaging the surface of the object 10. The image of the surface may be used to reposition the probe 20 and/or to electronically steer the beam(s) from the probe 20 as appropriate.

At stage 114, the sound transducer elements 16 are excited to produce a desired sound beam directed at the object 10. The computer 30 selects one or more desired transducer elements for transmitting energy to provide the desired direction, coverage, and energy of the sound energy to provide sufficient energy to a desired region or point to achieve desired results (e.g., for diagnosis, imaging, and/or therapy). The computer 30 regulates the frequency, phase, amplitude, and delay of the energy provided by the selected sound transducer elements. The delay from element to element may vary to provide an electrically-controlled beam direction such that desired amounts of energy from the array as a whole, and/or individual element, are incident upon the object 10 and are directed to reach a desired region in the object 10.

In one implementation, the sound energy is provided in a coded manner, with the energy being pulsed over a range of frequencies, with power magnitudes that vary in accordance with (depending on) the frequency of the signal transmitted. The beam may be broad or focused. Elements may also be selected and excited to provide sound waves at an individual level to enhance characterization of the object 10.

Stage 112 and/or 114 may be repeated depending upon the application. For example, for imaging, the probe 10 may be repositioned mechanically and/or the direction of the sound beam electronically steered to cover the entire area to be diagnosed.

At stage 116, for diagnostic or imaging applications, the computer 30 processes received sound reflections to determine appropriate characteristics of the tooth 10. The computer 30 may manipulate the returned reflections and compare the reflections to known indicias in a database to determine one or more properties, such as a determination of a cavity within the object 10.

In sum, the accelerometer 96 digitizes the vibrations and inputs them into the computer 98. The software 100 in the computer then compares these inputs to known files of data relating to vibrations. The computer 98 displays a response on the computer screen for that patient. If there are multiple states those will be displayed. If there are ambiguous outcomes, probabilities will be given.

Next, various experiments and experimental results are discussed. These experiments test if a dental professional can pick out the differences in sound outputs between various types of teeth.

Figure 5A:
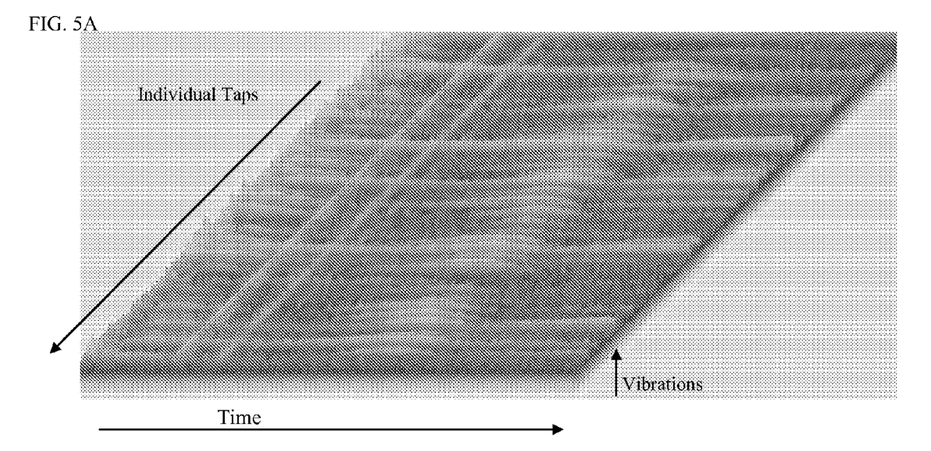
FIG. 5 shows an exemplary process to use the system of FIG. 1
Figure 5B:
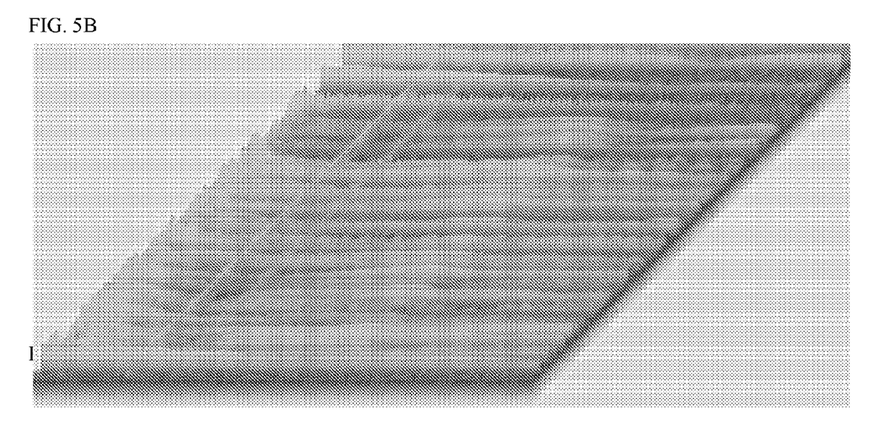
Figure 6:
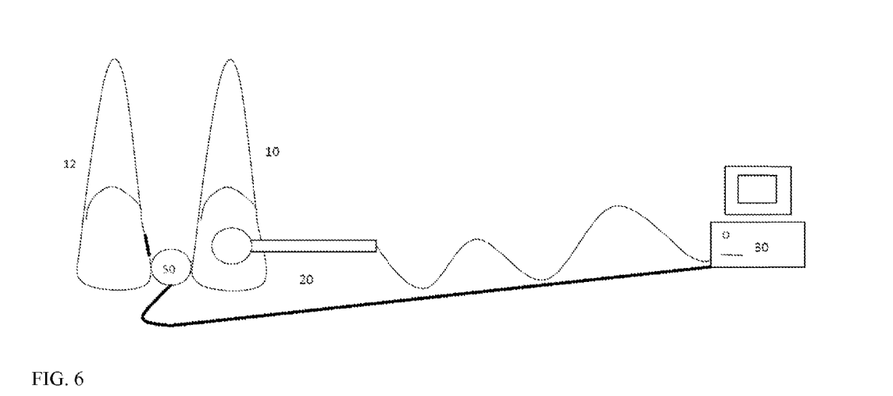
FIG. 6 shows an exemplary system to diagnose a patient.

One subject with full upper dentition was used to for data gathering. A tap was placed on a tooth and an accelerometer device was placed on the tooth in question. A tap was done on a known healthy tooth; the canine and the vibrations picked up on the teeth being examined. The accelerometer device feeds information into a computer where a Fourier transfer waterfall graph is plotted (FIGS. 5A-5B). A waterfall plot simply is a display of a 10-20 taps in a row and the outcomes displayed in a way that each graph is visible. Five plots each one of a porcelain crown and one of a natural tooth were obtained. Four dental professionals were asked if they could tell the difference between the 10 plots.

FIGS. 5A-5B show exemplary Fourier transfer waterfall plots from two different teeth. One tooth is a natural central incisor where ten experiments with data were collected and printed out for professionals to review, five experiments with the natural tooth and five with the porcelain tooth. Four blinded subjects were asked to pick from ten of these plots lettered A-J. The results of that experiment are given below:

| | Subject Image: | | | | | | | | | |
|---|---|---|---|---|---|---|---|---|---|---|
| | A | B | C | D | E | F | G | H | I | J |
| C Correct | 1 | 1 | 1 | 1 | 1 | 1 | 1 | 1 | 1 | 1 |
| C Incorrect | 0 | 0 | 0 | 0 | 0 | 0 | 0 | 0 | 0 | 0 |
| N Correct | 1 | 1 | 1 | 1 | 1 | 1 | 1 | 1 | 1 | 1 |
| N Incorrect | 0 | 0 | 0 | 0 | 0 | 0 | 0 | 0 | 0 | 0 |
| R Correct | 1 | 1 | 1 | 1 | 1 | 1 | 1 | 1 | 1 | 1 |
| R Incorrect | 0 | 0 | 0 | 0 | 0 | 0 | 0 | 0 | 0 | 0 |
| D Correct | 1 | 1 | 1 | 1 | 1 | 1 | 1 | 1 | 1 | 1 |
| D Incorrect | 0 | 0 | 0 | 0 | 0 | 0 | 0 | 0 | 0 | 0 |

All subjects were able to identify what image represented what tooth. The statistic used to analyze agreement is kappa (1):

$$\kappa = \frac{\overline{P} - \overline{P}_e}{1 - \overline{P}_e}$$

The kappa statistic analyzes the agreement of multiple subjects viewing a serious of objects. If the raters are in complete agreement then kappa=1. If there is no agreement among the raters (other than what would be expected by chance) then kappa<=0. There was 100% agreement between the reviewers of the graphs.

Four professionals who have looked at the ten graphs of FIGS. 5A-5B were able to see the differences in the displayed data with 100% accuracy. For these professionals, the software can also be used to analyze the data and provide feedback on dental situations such as disease states or whether the tooth is natural or artificial based on the reflected vibrations and subsequent analysis.

The invention may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device.

By way of example, a digital receiver is discussed next. The digital receiver is essentially a computer with transceivers that can be wired or wireless. The computer preferably includes a processor, random access memory (RAM), a program memory (preferably a writable read-only memory (ROM) such as a flash ROM) and an input/output (I/O) controller coupled by a CPU bus. The computer may optionally include a hard drive controller which is coupled to a hard disk and CPU bus. Hard disk may be used for storing application programs, such as the present invention, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link. Optionally, a display, a keyboard and a pointing device (mouse) may also be connected to I/O bus. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

Each computer program is tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A dental diagnostic system, comprising
   a. a vibratory transducer adapted to be coupled to a dental object to induce vibrations in the dental object;
   b. a receiver adapted to be coupled to a second dental object to pick up delayed vibrations transmitted by the vibratory transducer;
   c. a processor coupled to the receiver and configured to process captured vibrations, to detect type of tooth including Central Incisor, Lateral Incisor, Canine, Bicuspid and Molar, to detect a presence of one or more dental materials on the tooth, to compare the captured vibrations against a database of known dental characteristics and to generate a diagnostic.

2. The system of claim 1, wherein the dental object comprises a tooth.

3. The system of claim 1, wherein the receiver comprises an accelerometer.

4. The system of claim 1, wherein the processor is coupled to the vibratory transducer and configured to regulate frequency, phase, amplitude, and delay of energy provided by the vibratory transducer.

5. The system of claim 1, wherein the vibratory transducer and receiver are housed in a mouthpiece or an appliance.

6. The system of claim 1, wherein the vibratory transducer comprises a solenoid with a diaphragm in contact with a rod and wherein the vibratory transducer is suspended by springs.

7. The system of claim 6, wherein the vibratory transducer has an adjustable frequency range.

8. The system of claim 1, wherein the database is configured to store known reflections of restorations, disease states, and tissues.

9. A dental diagnostic method, comprising
a. inducing vibrations in a first dental object using a vibratory transducer;
b. picking up at a receiver vibrations transmitted by the vibratory transducer from a second dental object and comparing the captured vibrations against a database of known dental characteristics, type of tooth including Central Incisor, Lateral Incisor, Canine, Bicuspid and Molar, and type of dental material on the tooth; and
c. generating a dental diagnostic using a processor and correcting dental deficiencies based on the diagnostic.

10. The method of claim 9, wherein the dental object comprises a tooth.

11. The method of claim 9, wherein the dental object comprises tissue.

12. The method of claim 9, wherein the vibratory transducer comprises a piezoelectric transducer.

13. The method of claim 9, wherein the receiver comprises an accelerometer.

14. The method of claim 9, wherein the processor is coupled to the vibratory transducer and configured to regulates frequency, phase, amplitude, and delay of energy provided by the vibratory transducer.

15. The method of claim 9, wherein the vibratory transducer and receiver are housed in a mouthpiece or an appliance.

16. The method of claim 9, wherein the vibratory transducer comprises a solenoid with a diaphragm in contact with a rod and wherein the vibratory transducer is suspended by springs.

17. The method of claim 16, wherein the vibratory transducer has an adjustable frequency range.

18. The method of claim 9, comprising processing captured vibration information to form an image or an anatomy of the object.

19. The method of claim 9, wherein the first and second dental objects are part of one tooth.

20. The method of claim 9, wherein the first and second dental objects comprise portions of two separate teeth.

\* \* \* \* \*